United States Patent
Heil et al.

(10) Patent No.: US 6,403,622 B1
(45) Date of Patent: Jun. 11, 2002

(54) PHENYLACETIC ACID HETEROCYCLYL AMIDES HAVING AN INSECTICIDAL EFFECT

(75) Inventors: Markus Heil, Leichlingen; Hans-Christian Militzer, Odenthal; Thomas Bretschneider, Lohmar; Bernd Alig, Königswinter; Astrid Mauler-Machnik, Leichlingen; Klaus Stenzel, Düsseldorf; Ulrike Wachendorff-Neumann, Neuwied, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/806,430

(22) PCT Filed: Sep. 23, 1999

(86) PCT No.: PCT/EP99/07105

§ 371 (c)(1),
(2), (4) Date: Apr. 27, 2001

(87) PCT Pub. No.: WO00/20415

PCT Pub. Date: Apr. 13, 2000

(30) Foreign Application Priority Data

Oct. 6, 1998 (DE) .......................... 198 46 008

(51) Int. Cl.[7] .................. C07D 417/12; A01N 43/08
(52) U.S. Cl. ............. 514/361; 514/372; 548/128; 548/214
(58) Field of Search ............... 548/214, 128; 514/361, 372

(56) References Cited

U.S. PATENT DOCUMENTS

| 3,816,421 A | 6/1974 | Gibbons et al. ...... 260/256.4 F |
| 5,538,939 A | 7/1996 | Muenster et al. ........... 504/269 |

FOREIGN PATENT DOCUMENTS

| CA | 2039955 | 10/1991 |
| EP | 0264217 | 4/1988 |
| EP | 0276196 | 7/1988 |
| EP | 0559612 | 9/1993 |
| EP | 0623282 | 11/1994 |
| EP | 0661281 | 7/1995 |
| WO | 93/19054 | 9/1993 |
| WO | 94/21617 | 9/1994 |
| WO | 95/31448 | 11/1995 |
| WO | 97/18198 | 5/1997 |
| WO | 97/26251 | 7/1997 |
| WO | 98/02424 | 1/1998 |
| WO | 98/05670 | 2/1998 |
| WO | 98/46592 | 10/1998 |

OTHER PUBLICATIONS

J. Chem. Soc., (month unavailable), 1956, pp. 404–414, J.W. Baker et al, "Mechanism of Aromatic Side–chain Reactions with Special Reference to the Polar Effects of Substituents. Part XVI. Hyperconjugation of Groups of the Type $CH_2X$ in the Benzaldehyde–Cyanohydrin Equilibria".

J. Het. Chem, 26, (month unavailable), 1989, pp. 1675–1578, R.E. Hackler et al, "The Syntheses of 5–Amino–3–t–butylisothiazole".

Monatshefte für Chemie, Bd. 85/1, (month unavailable), 1954, pp. 80–87, L. Schmid et al, "Synthese von p–Acetylphenyl–fettsäuren, p–[(α)–Oxyäthylphenyl]–fettsäuren, der p–Methylatrolactinsäure und des Dehydrocholsäureamids des p–Aminoacetophenons".

Gazz. Chim. Ital. 107, (month unavailable), 1977, pp. 1–5, L. Pentimalli, et al, "Imidazo[1,2–d]–1,2,4–Thiadiazoles".

*Primary Examiner*—Robert Gerstl
(74) *Attorney, Agent, or Firm*—Joseph C. Gil

(57) ABSTRACT

Novel phenylacetic acid heterocyclyl amides of the formula

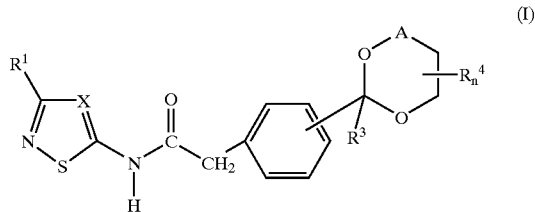

(I)

in which
$R^1$, $R^2$, $R^3$, $R^4$, A, X and n are as defined in the description, a process for preparing these novel compounds and their use for controlling undesirable microorganisms and animal pests.

Novel intermediates of the formula

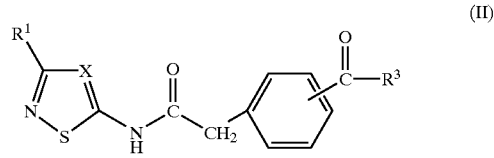

(II)

and a plurality of processes for their preparation.

16 Claims, No Drawings

PHENYLACETIC ACID HETEROCYCLYL AMIDES HAVING AN INSECTICIDAL EFFECT

FIELD OF THE INVENTION

The present invention relates to novel phenylacetic acid heterocyclyl amides, to a process for their preparation and to their use for controlling undesirable microorganisms and animal pests.

BACKGROUND OF THE INVENTION

It is already known that numerous N-(5-isothiazolyl)-amides or N-(5-thiadiazolyl)-amides have insecticidal and fungicidal properties (cf. WO 97-18 198, WO 97-26 251 and WO 95-31 448). The activity of these substances is good; however, it is sometimes unsatisfactory at low application rates.

SUMMARY OF THE INVENTION

Phenylacetic acid heterocyclyl amides of the formula

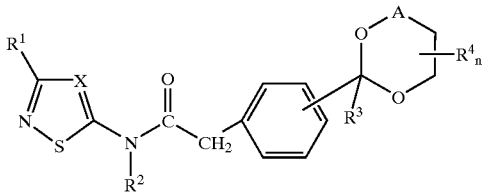

may be used to control microorganisms and animal pest.

DETAILED DESCRIPTION

This invention, accordingly, provides novel phenylacetic acid heterocyclyl amides of the formula

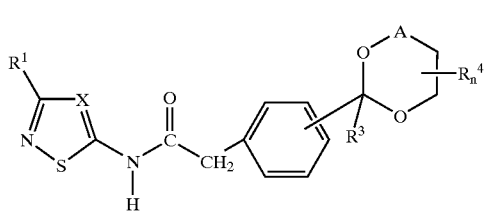

in which
R$^1$ represents alkyl, halogenoalkyl, alkoxyalkyl, alkylthioalkyl, alkoxy, alkylthio or represents optionally substituted cycloalkyl,
R$^2$ represents hydrogen, alkylcarbonyl, alkoxycarbonyl or represents in each case optionally substituted arylcarbonyl, aryloxycarbonyl or aralkyloxycarbonyl,
R$^3$ represents hydrogen or alkyl,
R$^4$ represents optionally substituted alkyl, optionally substituted alkenyl, optionally substituted alkinyl, optionally substituted aryl, optionally substituted aralkyl, optionally substituted aralkyloxy or represents optionally substituted aralkyloxyalkyl, or two geminal or vicinal R$^4$ radicals together with the carbon atom(s) to which they are attached form a saturated or unsaturated, optionally substituted five-or six-membered ring which may contain one or two hetero atoms,
n represents integers from 1 to 4,
x represents a nitrogen atom or represents a grouping of the formula CH, C—Cl, C—Br, C—C≡CH, C—CN
or

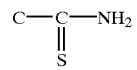

and
A represents a direct bond or a CH$_2$ group.
Furthermore, it has been found that phenylacetic acid heterocyclyl amides of the formula (I) can be prepared by
a) reacting amino derivatives of the formula

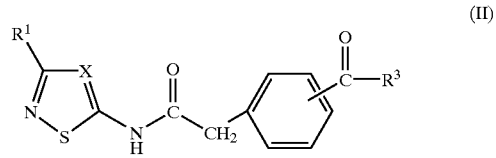

in which
R$^1$, R$^3$ and X are as defined above,
with diols of the formula

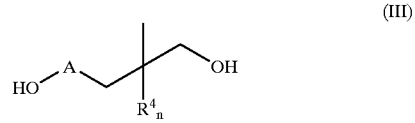

in which
A, R$^4$ and n are as defined above,
if appropriate in the presence of a diluent and in the presence of a dehydrating agent
and
b) if appropriate, reacting the resulting phenylacetic acid heterocyclyl amides of the formula

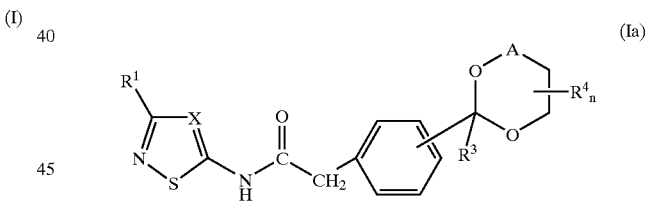

in which
R$^1$, R$^3$, R$^4$, A, X and n are as defined above,
with acid halides of the formula

in which
Hal represents chlorine or bromine and
R$^5$ represents alkyl, alkoxy or represents in each case optionally substituted aryl, aryloxy or aralkyloxy,
in the presence of a diluent and in the presence of an acid binder.

Finally, it has been found that the phenylacetic acid heterocyclyl amides of the formula (I) are highly suitable for controlling undesirable microorganisms and animal pests.

Surprisingly, the compounds according to the invention have significantly better fungicidal and insecticidal activity than the constitutionally most similar priort-art compounds of the same direction of action.

The formula (I) provides a general definition of the phenylacetic acid heterocyclyl amides according to the invention.

R$^1$ preferably represents C$_1$–C$_4$-alkyl, C$_1$–C$_4$-halogenoalkyl having 1 to 5 fluorine, chlorine and/or bromine atoms, represents C$_1$–C$_4$-alkoxy-C$_1$–C$_4$-alkyl, C$_1$–C$_4$-alkylthio-C$_1$–C$_4$-alkyl, C$_1$–C$_4$-alkoxy, C$_1$–C$_4$-alkylthio or represents C$_3$–C$_6$-cycloalkyl which is optionally mono- to trisubstituted by identical or different substituents from the group consisting of C$_1$–C$_4$-alkyl and halogen.

R$^2$ preferably represents hydrogen, C$_1$–C$_4$-alkyl-carbonyl, C$_1$–C$_4$-alkoxy-carbonyl or represents phenyl-carbonyl, phenyloxy-carbonyl or phenyl-C$_1$–C$_4$-alkyloxy-carbonyl, where the three last mentioned radicals may be mono- to trisubstituted in the phenyl moiety by identical or different substituents from the group consisting of halogen, nitro, cyano, C$_1$–C$_4$-alkyl, C$_1$–C$_4$-alkoxy, C$_1$–C$_4$-alkylthio, halogenoalkyl having 1 or 2 carbon atoms and 1 to 5 identical or different halogen atoms, halogenoalkoxy having 1 or 2 carbon atoms and 1 to 5 identical or different halogen atoms and/or halogenoalkylthio having 1 or 2 carbon atoms and 1 to 5 identical or different halogen atoms.

R$^3$ preferably represents hydrogen or C$_1$–C$_4$-alkyl.

R$^4$ preferably represents C$_1$–C$_{12}$-alkyl, C$_1$–C$_8$-halogenoalkyl having 1 to 8 identical or different halogen atoms, C$_1$–C$_4$-hydroxyalkyl, C$_2$–C$_8$-halogenoalkenyl having 1 to 8 identical or different halogen atoms, C$_2$–C$_8$alkinyl, C$_2$–C$_8$-halogenoalkinyl having 1 to 8 halogen atoms, C$_1$–C$_8$-alkoxy-C$_1$–C$_4$-alkyl, C$_2$–C$_8$-alkenoxy-C$_1$–C$_4$-alkyl, C$_2$–C$_8$-alkinoxy-C$_1$–C$_4$-alkyl, C$_1$–C$_8$-halogenoalkoxy-C$_1$–C$_4$-alkyl having 1 to 8 identical or different halogen atoms, C$_2$–C$_8$-halogenoalkenyloxy-C$_1$–C$_4$-alkyl having 1 to 8 identical or different halogen atoms, C$_2$–C$_8$-halogenoalkinyloxy-C$_1$–C$_4$-alkyl having 1 to 8 identical or different halogen atoms, C$_1$–C$_8$-alkoxycarbonyl-C$_1$–C$_4$-alkyl, C$_4$–C$_8$-alkylcarbonyloxy-C$_1$–C$_4$-alkyl, C$_1$–C$_8$-halogenoalkyl-carbonyloxy-C$_1$–C$_4$-alkyl having 1 to 8 identical or different halogen atoms, C$_1$–C$_8$-alkylthio-C$_1$–C$_4$-alkyl, or represents phenyl, phenylalkyl having 1 to 4 carbon atoms in the alkyl moiety, phenylalkoxy having 1 to 4 carbon atoms in the alkoxy moiety or represents phenylalkyloxyalkyl having 1 to 4 carbon atoms in the alkyl moiety and 1 to 4 carbon atoms in the oxyalkyl moiety, where the four last mentioned radicals may be mono- to trisubstituted in the phenyl moiety by identical or different substituents from the group consisting of halogen, nitro, cyano, C$_1$–C$_4$-alkyl, C$_1$–C$_4$-alkoxy, C$_1$–C$_4$-alkylthio, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkylsulfinyl having 1 to 4 carbon atoms, alkylsulfonyl having 1 to 4 carbon atoms, alkylcarbonyl having 1 to 4 carbon atoms in the alkyl moiety and alkoxycarbonyl having 1 to 4 carbon atoms in the alkoxy moiety.

Moreover, two geminal or vicinal R$^4$ radicals together with the carbon atom(s) to which they are attached preferably represent a saturated or unsaturated five- or six-membered ring which may contain one or two oxygen, sulfur and/or nitrogen atoms and which may be mono- or disubstituted by halogen, alkyl having 1 to 4 carbon atoms and/or alkoxy having 1 to 4 carbon atoms.

n preferably represents 1, 2 or 3.

X preferably represents a nitrogen atom or represents a grouping of the formula CH, CCl, CBr, C—CN, C—C≡CH or

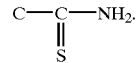

A also preferably represents a direct bond or represents a CH$_2$ group.

R$^1$ particularly preferably represents methyl, ethyl, propyl, isopropyl, n-butyl, i-butyl, sec-butyl, tert-butyl, halogenoalkyl having 1 or 2 carbon atoms and 1 to 3 fluorine, chlorine, and/or bromine atoms, alkoxyalkyl having 1 or 2 carbon atoms in the alkoxy moiety and 1 or 2 carbon atoms in the alkyl moiety, alkylthioalkyl having 1 or 2 carbon atoms in the alkylthio moiety and 1 or 2 carbon atoms in the alkyl moiety, methoxy, ethoxy, methylthio, ethylthio or represents cyclopentyl, cyclohexyl or cyclopropyl, optionally mono- or disubstituted by methyl, ethyl, fluorine and/or chlorine.

R$^2$ particularly preferably represents hydrogen, methylcarbonyl, ethylcarbonyl, methoxycarbonyl, ethoxycarbonyl, propoxycarbonyl, isopropoxycarbonyl, butoxycarbonyl, i-butoxycarbonyl, sec-butoxycarbonyl, tert-butoxycarbonyl, phenylcarbonyl, phenyloxycarbonyl or phenylalkoxycarbonyl having 1 or 2 carbon atoms in the alkoxy moiety, where the three last mentioned radicals may be mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy and trifluoromethylthio.

R$^3$ particularly preferably represents hydrogen, methyl or ethyl.

R$^4$ particularly preferably represents C$_1$–C$_{10}$-alkyl, halogenoalkyl having 1 to 8 carbon atoms and 1 to 8 fluorine, chlorine and/or bromine atoms, hydroxyalkyl having 1 or 2 carbon atoms, C$_2$–C$_8$-alkenyl, C$_2$–C$_8$halogenoalkenyl having 1 to 8 fluorine, chlorine and/or bromine atoms, C$_2$–C$_8$-alkinyl, C$_2$–C$_8$-halogenoalkinyl having 1 to 8 fluorine, chlorine and/or bromine atoms, C$_1$–C$_8$-alkoxy-C$_1$–C$_2$-alkyl, C$_2$–C$_8$-alkenoxy-C$_1$–C$_2$-alkyl, C$_2$–C$_8$-alkinoxy-C$_1$–C$_2$-alkyl, C$_1$–C$_6$-halogenoalkoxy-C$_1$–C$_2$-alkyl having 1 to 5 fluorine, chlorine and/or bromine atoms, C$_2$–C$_6$-halogenoalkenyloxy-C$_1$–C$_2$alkyl having 1 to 5 fluorine, chlorine and/or bromine atoms, C$_2$–C$_6$halogenoalkinyloxy-C$_1$–C$_2$-alkyl having 1 to 5 fluorine, chlorine and/or bromine atoms, C$_1$–C$_8$-alkoxy-carbonyl-C$_1$–C$_2$-alkyl, C$_1$–C$_8$-alkyl-carbonyloxy-C$_1$–C$_2$-alkyl, C$_1$–C$_6$-halogenoalkyl-carbonyloxy-C$_1$–C$_2$-alkyl having 1 to 5 fluorine, chlorine and/or bromine atoms, C$_1$–C$_6$-alkylthio-C$_1$–C$_2$-alkyl or represents phenyl, phenylalkyl having 1 or 2 carbon atoms in the alkyl moiety, phenylalkoxy having 1 or 2 carbon atoms in the alkoxy moiety or represents phenylalkyl-oxyalkyl having 1 or 2 carbon atoms in the alkyl moiety and 1 or 2 carbon atoms in the oxyalkyl moiety, where the four last mentioned radicals may be mono- to trisubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy, trifluoromethylthio, methylsulfinyl, methylsulfonyl, methylcarbonyl, ethylcarbonyl, methoxycarbonyl and/or ethoxycarbonyl.

Moreover, two geminal or vicinal $R^4$ radicals together with the carbon atoms(s) to which they are attached particularly preferably represent a saturated or monounsaturated six-membered ring which may contain one or two oxygen, sulfur and/or nitrogen atoms and which may be mono- or disubstituted by fluorine, chlorine, methyl, ethyl and/or methoxy.

n particularly preferably represents 1 or 2.

x particularly preferably represents a nitrogen atom or represents a grouping of the formula CH, CCl, CBr, C—CN, C—C≡CH or

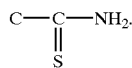

A also particularly preferably represents a direct bond or represents a $CH_2$ group.

$R^1$ very particularly preferably represents methyl, ethyl, chloromethyl, difluoromethyl, trifluoromethyl, methoxymethyl, ethoxymethyl, methylthiomethyl, methoxy, ethoxy, methylthio, cyclopropyl, cyclopentyl or cyclohexyl.

$R^2$ very particularly preferably represents hydrogen, methylcarbonyl, ethylcarbonyl, methoxycarbonyl, ethoxycarbonyl, phenylcarbonyl, phenyloxycarbonyl or phenylmethoxycarbonyl, where the three last mentioned radicals may be mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy and trifluoromethylthio.

$R^3$ very particularly preferably represents hydrogen or methyl.

$R^4$ very particularly preferably represents $C_1$–$C_{10}$-alkyl, halogenoalkyl having 1 to 4 carbon atoms and 1 to 5 fluorine, chlorine and/or bromine atoms, hydroxymethyl, hydroxyethyl, $C_2$–$C_6$-alkenyl, $C_2$–$C_6$-halogenoalkenyl having 1 to 5 fluorine, chlorine and/or bromine atoms, $C_2$–$C_6$-alkinyl, $C_2$–$C_6$halogenoalkinyl having 1 to 5 fluorine, chlorine and/or bromine atoms, $C_1$–$C_6$-alkoxy-methyl, $C_2$–$C_6$-alkenoxy-methyl, $C_2$–$C_6$-alkinoxy-methyl, $C_1$–$C_4$-halogenoalkoxy-methyl having 1 to 3 fluorine, chlorine and/or bromine atoms, $C_2$–$C_4$-halogenoalkenyloxy-methyl having 1 to 3 fluorine, chlorine and/or bromine atoms, $C_2$–$C_4$-halogenoalkinyloxy-methyl having 1 to 3 fluorine, chlorine and/or bromine atoms, $C_1$–$C_4$-alkoxycarbonyl-methyl, $C_1$–$C_4$-alkyl-carbonyloxy-methyl, $C_1$–$C_4$-halogenoalkyl-carbonyloxy-methyl having 1 to 3 fluorine, chlorine and/or bromine atoms, $C_1$–$C_4$-alkylthio-methyl, or represents phenyl, phenylalkyl having 1 or 2 carbon atoms in the alkyl moiety, phenylalkoxy having 1 or 2 carbon atoms in the alkoxy moiety or represents phenylmethyl-oxymethyl, where the four last mentioned radicals may be mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy, trifluoromethylthio, methylsulfinyl, methylsulfonyl, methylcarbonyl, ethylcarbonyl, methoxycarbonyl and ethoxycarbonyl.

Moreover, two geminal or vicinal $R^4$ radicals together with the carbon atom(s) to which they are attached very particularly preferably represent a saturated or monounsaturated six-membered ring which may contain one or two non-adjacent oxygen atoms and which may be mono- or disubstituted by fluorine, chlorine, methyl, ethyl and/or methoxy.

n very particularly preferably represents 1 or 2.

X very particularly preferably represents a nitrogen atom or represents a grouping of the formula CH, CCl, CBr, C—CN, C—C≡CH or

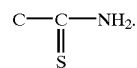

A also very particularly preferably represents a direct bond or represents a $CH_2$ group.

The radical definitions mentioned above can be combined with one another as desired. Moreover, individual definitions may not apply.

Examples of phenylacetic acid heterocyclyl amides of the formula (I) according to the invention which may be mentioned are the compounds listed in the tables below.

TABLE 1

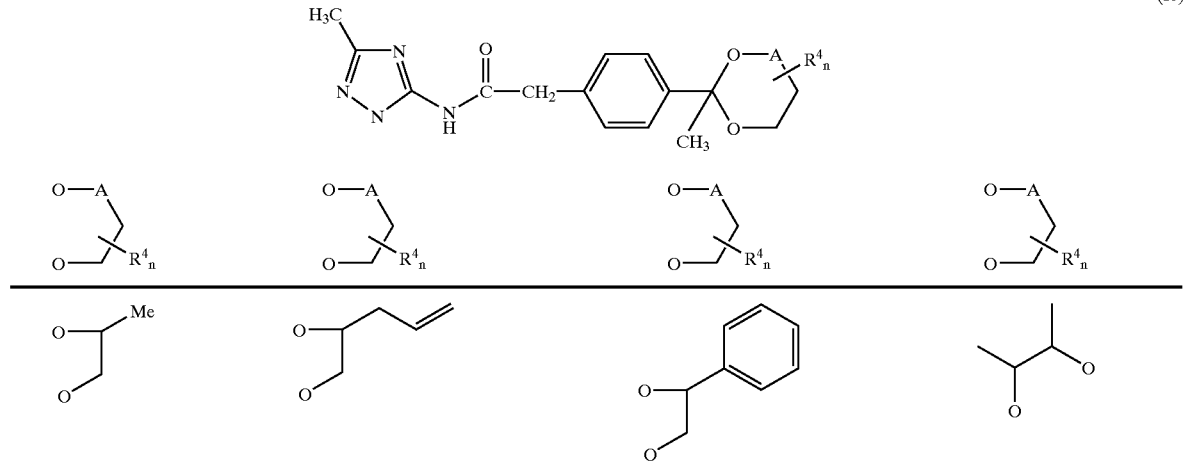

TABLE 1-continued
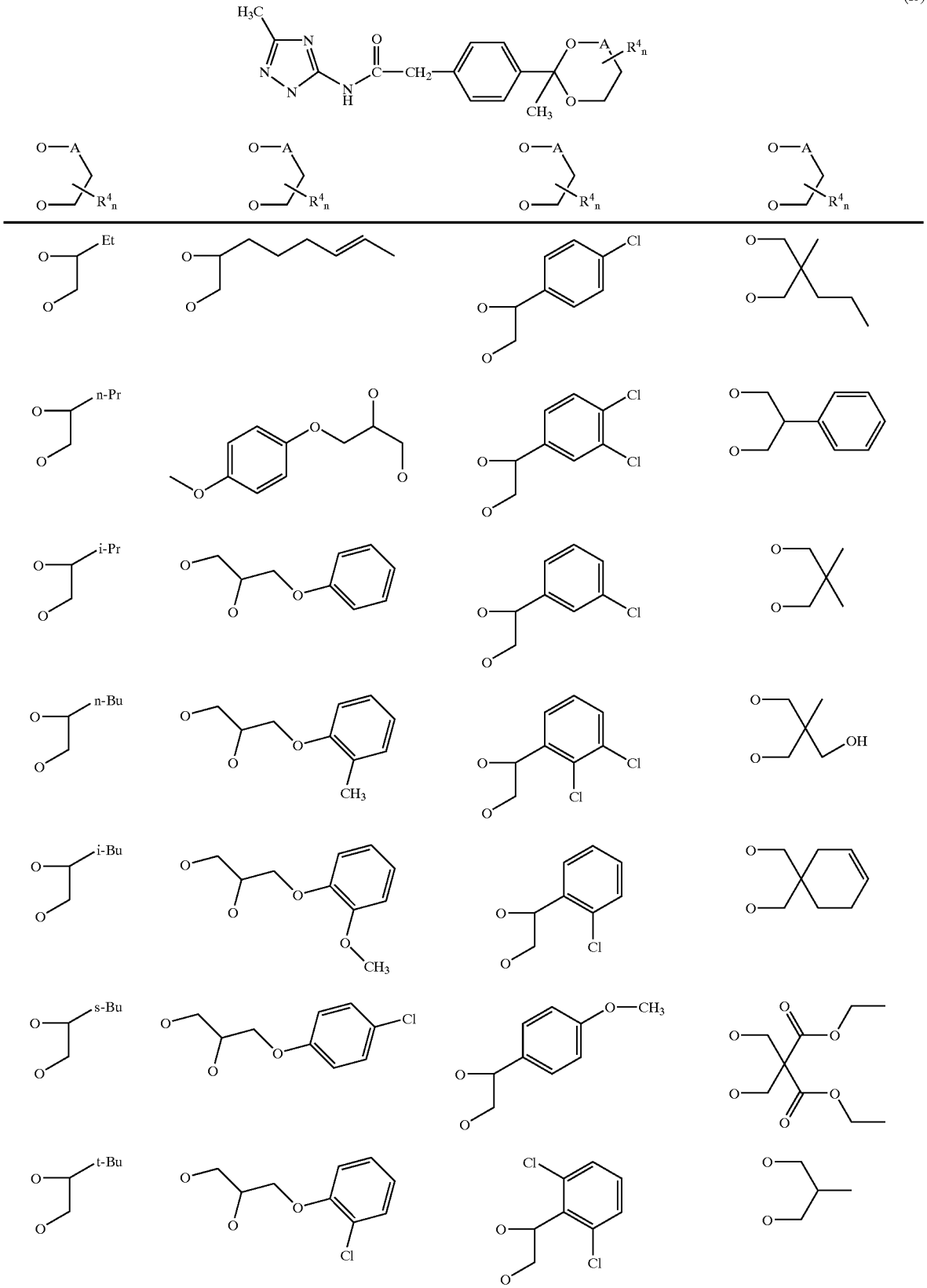

TABLE 1-continued
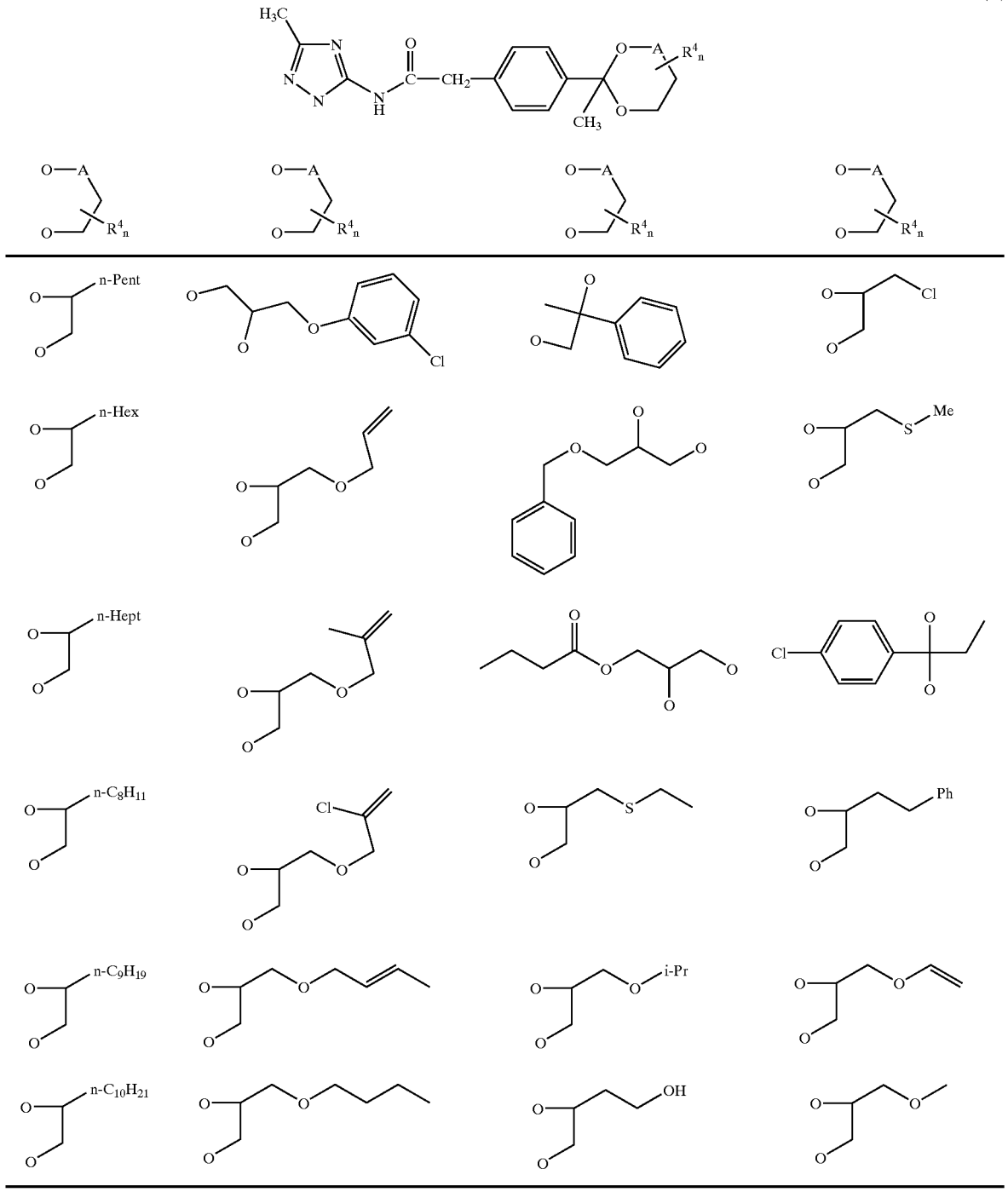
In this table:
Me = methyl
Et = ethyl
Pr = propyl
Bu = butyl
Pent = pentyl
Hex = hexyl
Hept = heptyl
Ph = phenyl

TABLE 2

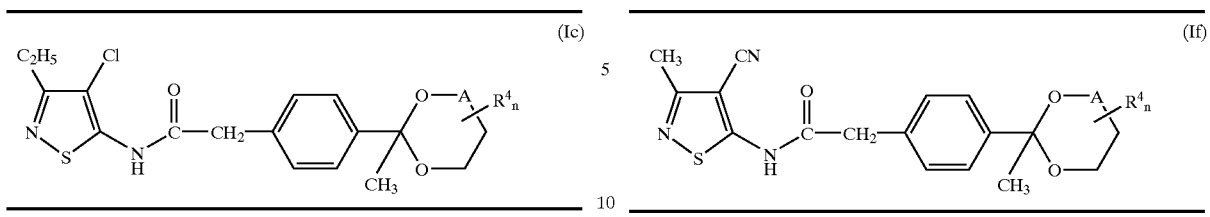
(Ic)

in which the structural unit

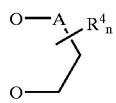

has the meanings given in Table 1.

TABLE 3

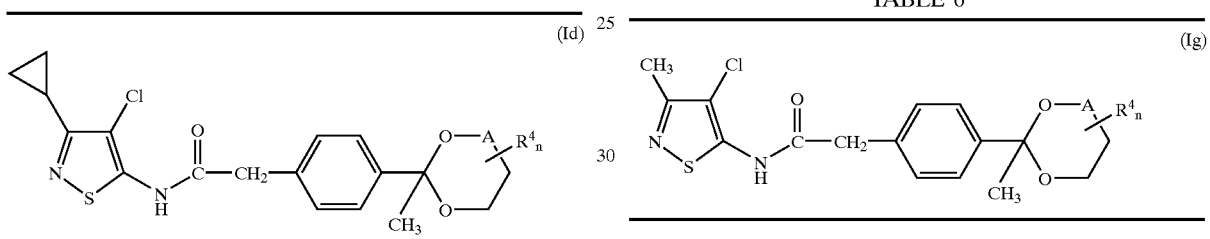
(Id)

in which the structural unit

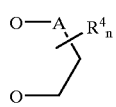

has the meanings given in Table 1.

TABLE 4

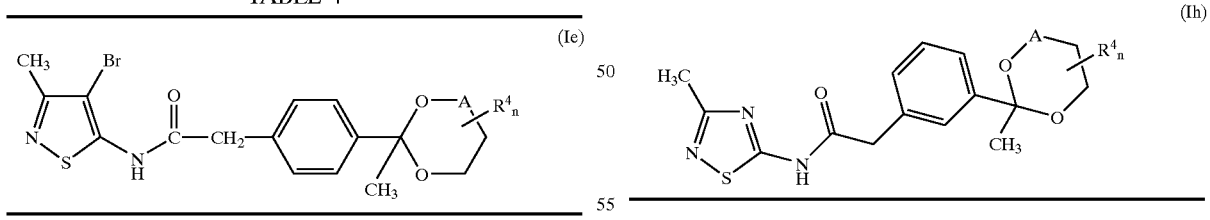
(Ie)

in which the structural unit

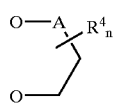

has the meanings given in Table 1.

TABLE 5

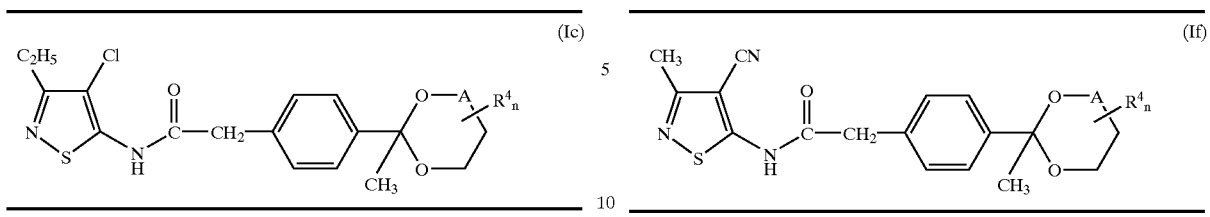
(If)

in which the structural unit

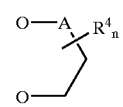

has the meanings given in Table 1.

TABLE 6

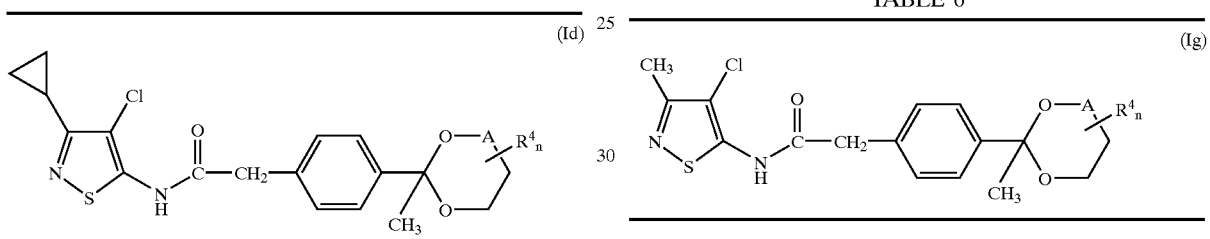
(Ig)

in which the structural unit

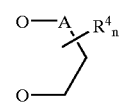

has the meanings given in Table 1.

TABLE 7

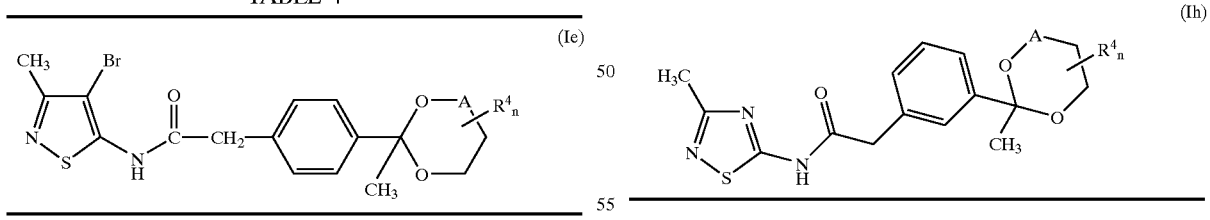
(Ih)

in which the structural unit

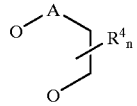

has the meaning given in Table 1.

TABLE 8

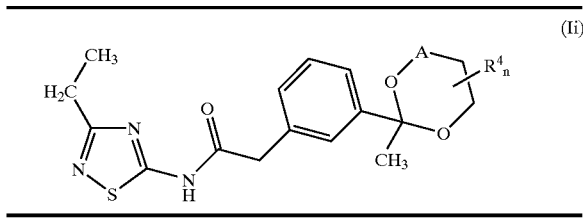
(Ii)

in which the structural unit

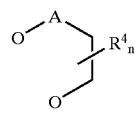

has the meaning given in Table 1.

TABLE 9

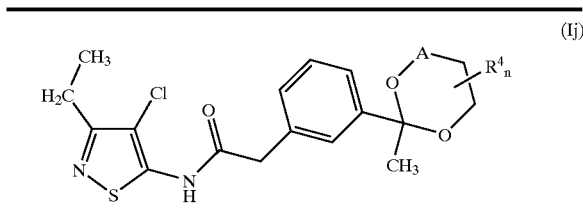
(Ij)

in which the structural unit

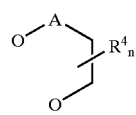

has the meaning given in Table 1.

TABLE 10

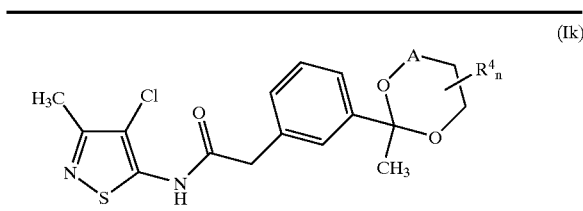
(Ik)

in which the structural unit

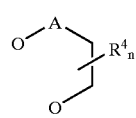

has the meaning given in Table 1.

TABLE 11

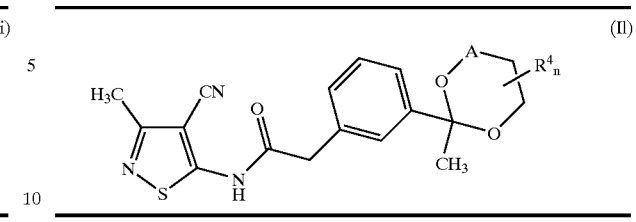
(Il)

in which the structural unit

has the meaning given in Table 1.

TABLE 12

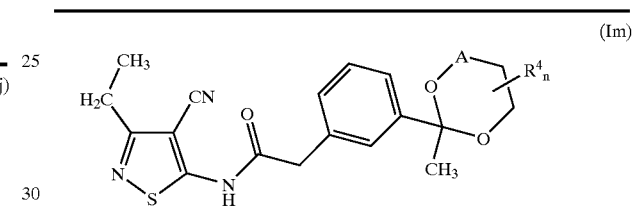
(Im)

in which the structural unit

has the meaning given in Table 1.

Using 5-(4-acetyl-phenyl)-acetylamino-4-chloro-3-methyl-isothiazole and 1,2-decanediol as starting materials, the course of the reaction of the process (a) according to the invention can be illustrated by the formula scheme below.

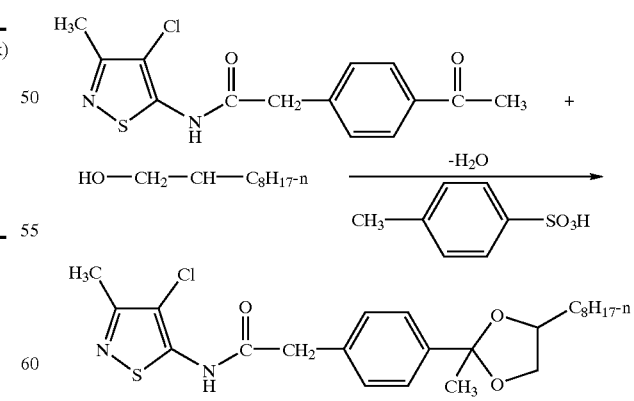

Using the reaction product of the equation given above as starting material and acetyl chloride as reaction component, the course of the process (b) according to the invention can be illustrated by the formula scheme below.

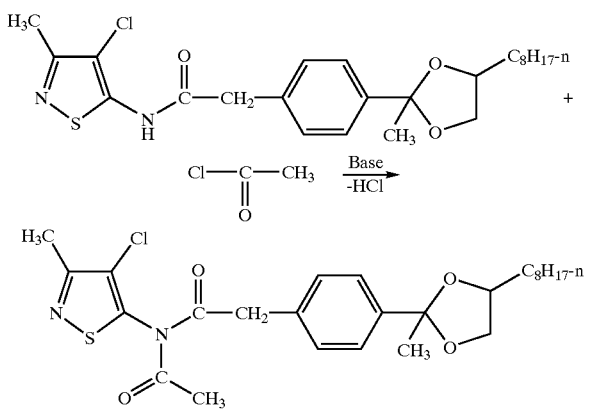

The formula (II) provides a general definition of the amino derivatives required as starting materials for carrying out the process (a) according to the invention. In this formula, $R^1$, $R^3$ and X preferably have those meanings which have already been mentioned in connection with the description of the compounds of the formula (I) according to the invention as being preferred for these radicals.

The amino derivatives of the formula (II) have hitherto not been disclosed. They can be prepared by c) reacting heterocyclyl-amines of the formula

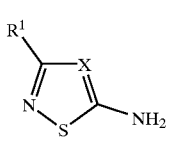

(V)

in which
$R^1$ and X are as defined above,
either
α) with acid halides of the formula

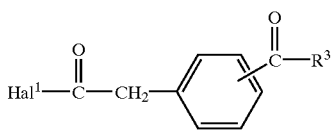

(VI)

in which
$R^3$ is as defined above and
$Hal^1$ represents chlorine or bromine,
if appropriate in the presence of an acid binder and if appropriate in the presence of a diluent,
or
β) with phenylacetic acid derivatives of the formula

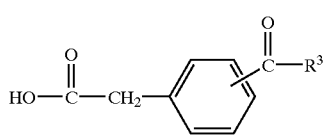

(VII)

in which
$R^3$ is as defined above,
in the presence of a catalyst and in the presence of a diluent.

The formula (V) provides a general definition of the heterocyclyl-amines required as starting materials for carrying out the process (c). In this formula, $R^1$ and X preferably have those meanings which have already been mentioned in connection with the description of the compounds of the formula (I) according to the invention as being preferred for these radicals.

The heterocyclyl-amines of the formula (V) are known or can be prepared by known methods (cf. DE-A 4 328 425, DE-A 2 249 162, WO 93-19 054, WO 94-21 617, J. Het. Chem. 26, 1575 (1989), Gazz. Chim. Ital. 107, 1 (1977), Chem. Ber. 195, 57 and EP-A 0 455 356).

The formula (VI) provides a general definition of the acid halides required as reaction components for carrying out the process (c, variant a). In this formula $R^3$ preferably has those meanings which have already been mentioned in connection with the description of the substances of the formula (I) according to the invention as being preferred for this radical. $Hal^1$ preferably represents chlorine.

The acid halides of the formula (VI) are known or can be prepared by known methods (cf. Monatsh. Chem. 85, 80 (1954) and J. Chem. Soc. 1956, 404).

The formula (VII) provides a general definition of the phenylacetic acid derivatives required as reaction components for carrying out the process (c, variant β). In this formula, $R^3$ preferably has those meanings which have already been mentioned in connection with the description of the substances of the formula (I) according to the invention as being preferred for this radical.

The phenylacetic acid derivatives of formula (VII) are likewise known or can be prepared by known methods (cf. the publications mentioned above).

Suitable acid binders for carrying out the process (c, variant α) are all customary inorganic and organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate, furthermore ammonium hydroxide, ammonium acetate or ammonium carbonate, or tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (c, variant α) are all inert organic solvents. Preference is given to using aliphatic, alicyclic or aromatic hydrocarbons, such as petroleum ether, hexane, heptane, cyclohexane, methylcyclohexane, benzene, toluene, xylene or decaline; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulfoxides, such as dimethyl sulfoxide; sulfones, such as sulfolane.

When carrying out the process (c, variant α), the reaction temperatures can be varied within a relatively wide range. In general, the process is carried out at temperatures between −10° C. and +150° C., preferably between 0° C. and 100° C.

The process (c, variant α), like the process (c, variant β) and the processes (a) and (b) are generally carried out under atmospheric pressure. However, it is also possible to operate under elevated or reduced pressure.

When carrying out the process (c, variant α), in general an equimolar amount of acid halide and an equivalent amount or an excess of acid binder are employed per mole of heterocyclyl-amine of the formula (V). Work-up is effected using customary methods. In general, the reaction mixture is concentrated after the reaction has ended, the residue that remains is admixed with water and an organic solvent which is sparingly water-miscible, and the organic phase is separated off, washed, dried and concentrated. The product that remains can be freed by customary methods from any impurities that may be present.

Suitable catalysts for carrying out the process (c, variant β) are all customary reaction promoters which are suitable for activating the carboxyl group of the phenylacetic acid derivative of the formula (VII). Preference is given to using carbonyldiimidazole and di-cyclohexyl-carbodiimide. Furthermore, the reaction can also be carried out in the presence of water-binding agents.

Suitable diluents for carrying out the process (c, variant β) are all inert organic solvents which are customary for such reactions. Preference is given to using aliphatic, alicyclic or aromatic hydrocarbons, such as petroleum ether, hexane, heptane, cyclohexane, methylcyclohexane, benzene, toluene, xylene or decaline; halogenated hydrocarbons, such as chlorobenzene, dichlorobenzene, dichloromethane, chloroform, carbon tetrachloride, dichloroethane or trichloroethane.

When carrying out the process (c, variant β), the reaction temperatures can be varied within a certain range. In general, the process is carried out at temperatures between 0° C. and 80° C., preferably between 10° C. and 70° C.

When carrying out the process (c, variant β), in general an equimolar amount of phenylacetic acid derivative of the formula (VII) and an equimolar amount of catalyst are employed per mole of heterocyclyl-amine of the formula (V). However, it is also possible to employ an excess of one or the other component. Work-up is carried out by customary methods. In general, precipitated solid is filtered off with suction, the filtrate is concentrated under reduced pressure and the residue that remains is chromatographed.

The formula (III) provides a general definition of the diols required as reaction components for carrying out the process (a) according to the invention. In this formula, A, $R^4$ and n preferably have those meanings which have already been mentioned in connection with the description of the compounds of the formula (I) according to the invention as being preferred for these radicals or for this index.

The diols of the formula (III) are known or can be prepared by known methods.

Suitable diluents for carrying out the process (a) according to the invention are all inert organic solvents which are customary for such reactions. Preference is given to using aromatic hydrocarbons, such as benzene, toluene or xylene.

Suitable dehydrating agents for carrying out the process (a) according to the invention are all customary reagents capable of effecting dehydration. Preference is given to using acids, such as sulfuric acid or p-toluenesulfonic acid, and also drying agents, such as anhydrous silica gel or molecular sieves, furthermore orthoformic esters.

When carrying out the process (a) according to the invention, the reaction temperatures can likewise be varied within a relatively wide range. In general, the process is carried out at temperatures between 0° C. and 150° C., preferably between 10° C. and 130° C.

When carrying out the process (a) according to the invention, in general from 1 to 2 mol, preferably from 1 to 1.5 mol, of diol of the formula (III) and from 1 to 5 mol of dehydrating agent are employed per mole of amine derivative of the formula (II). Work-up is carried out by customary methods. In general, the reaction mixture is washed successively with water and an aqueous-basic solution and then concentrated under reduced pressure, and the product that remains is, if appropriate, freed by customary methods of any impurities that may still be present.

The phenylacetic acid heterocyclyl-amides of the formula (Ia) required as starting materials for carrying out the process (b) according to the invention are compounds according to the invention which can be prepared by process (a).

The formula (IV) provides a general definition of the acid halides required as reaction components for carrying out the process (b) according to the invention. In this formula, $R^5$ preferably represents $C_1$–$C_4$-alkyl, $C_1$–$C_4$-alkoxy, represents phenyl, phenyloxy or phenyl-$C_1$–$C_4$-alkyloxy, where the three lastmentioned radicals may be mono- to trisubstituted in the phenyl moiety by identical or different substituents from the group consisting of halogen, nitro, cyano, $C_1$–$C_4$-alkyl, $C_1$–$C_4$-alkoxy, $C_1$–$C_4$-alkylthio, halogenoalkyl having 1 or 2 carbon atoms and 1 to 5 identical or different halogen atoms, halogenoalkoxy having 1 or 2 carbon atoms and 1 to 5 identical or different halogen atoms and halogenoalkylthio having 1 or 2 carbon atoms and 1 to 5 identical or different halogen atoms.

$R^5$ particularly preferably represents methyl, ethyl, methoxy, ethoxy, propoxy, isopropoxy, butoxy, i-butoxy, sec-butoxy, tert-butoxy, phenyl, phenyloxy or phenylalkoxy having 1 or 2 carbon atoms in the alkoxy moiety, where the three lastmentioned radicals may be mono- or disubstituted in the phenyl moiety by identical or different substituents from the group consisting of fluorine, chlorine, bromine nitro, cyano, methyl, ethyl, methoxy, ethoxy, methylthio, ethylthio, chloromethyl, dichloromethyl, difluoromethyl, trifluoromethyl, trifluoromethoxy and trifluoromethylthio.

$R^5$ very particularly preferably represents methyl, ethyl, methoxy, ethoxy, phenyl, phenyloxy or phenylmethoxy, where the three lastmentioned radicals may be mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy and trifluoromethylthio.

The acid halides of the formula (IV) are known or can be prepared by known methods.

Suitable acid binders for carrying out the process (b) according to the invention are all customary inorganic and organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate, furthermore ammonium hydroxide, ammonium acetate or ammonium carbonate, or tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (b) according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decaline; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulfoxides, such as dimethyl sulfoxide; sulfones, such as sulfolane.

When carrying out the process (b) according to the invention, the reaction temperatures can be varied within a relatively wide range. In general, the process is carried out at temperatures between −10° C. and +150° C., preferably between 0° C. and 100° C.

When carrying out the process (b) according to the invention, in general from 1 to 2 mol of acid halide of the formula (IV) and an equivalent amount or an excess of acid binder are employed per mole of phenylacetic acid heterocyclyl-amide of the formula (Ia). Work-up is carried out by customary methods. In general, the reaction mixture is concentrated after the reaction has ended, the residue that remains is admixed with water and a poorly water-miscible organic solvent and the organic phase is separated off, washed, dried and concentrated. The product that remains can be freed by customary methods of any impurities that may be present.

The active compounds according to the invention can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases affecting cereals, such as mildew, and diseases in viticulture and fruit and vegetable growing, such as, for example, against Venturia, Podosphaera and Plasmopara species. They also have good in vitro action against Oomycetes.

In the protection of materials, the active compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms of the following genera may be mentioned as examples:

Alternaria, such as *Alternaria tenuis*,

Aspergillus, such as *Aspergillus niger*,

Chaetomium, such as *Chaetomium globosum*,

Coniophora, such as *Coniophora puetana*,

Lentinus, such as *Lentinus tigrinus*,

Penicillium, such as *Penicillium versicolor*,

Aureobasidium, such as *Aureobasidium pullulans*,

Sclerophoma, such as *Sclerophoma pityophila*,

Trichoderma, such as *Trichoderma viride*,

Escherichia, such as *Escherichia coli*,

Pseudomonas, such as *Pseudomonas aeruginosa*,

Staphylococcus, such as *Staphylococcus aureus*.

The active compounds according to the invention are also suitable for controlling animal pests, in particular insects, arachnids and nematodes, which are encountered in agriculture, in forests, in horticulture, in the protection of stored products and of materials, and in the hygiene or veterinary medicine sector, and have good plant tolerance and favorable toxicity to warm-blooded animals. The compounds are active against normally sensitive and resistant species and against pests in all or some stages of development. The abovementioned animal pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculate.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae,* Myzus spp., *Phorodon humuli, Rhopalosiphum padi,* Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds which can be used according to the invention can be employed with particularly good results for controlling plant-damaging mites, such as against the greenhouse red spider mite (*Tetranychus urticae*), or for controlling plant-damaging insects, such as against mercapatilis of the owlet moth (*Plutella maculipennis*), the larvae of the mustard beetle (*Phaedon cochleanrae*), and the green rice leafhopper (*Nephotettix cincticeps*).

The compounds which can be used according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example,. Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermnanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds according to the invention are also suitable for increasing the harvest yield. Moreover, they have low toxicity and are tolerated well by plants.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, bion, biphenyl, bitertanol, blasticidin-S, bromuconazole, bupirimate, buthiobate, calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulfate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeciam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinoxyfen, sulfur and sulfur preparations, tebuconazole, tecloflalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-bpropyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulfonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-tifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulfonyl]-5-(trichloromethyl)-1,3.4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzarnide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulfate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl-[(4-chlorophenyl)-azo]-cyanoacetate, potassium bicarbonate, methanetetrathiol-sodium salt, methyl-1-(2,3-dihydro-2,2-dimethyl-1H-inden-1-yl)-1H-imidazole-5-carboxylate, methyl-N-(2,6-dimethylphenyl)-N-(5-isoxazolylcarbonyl)-DL-alaninate, methyl -N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulfonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine-sodium salt, O,O-diethyl-[2-(dipropylamino)-2-oxoethyl]-ethylphosphoramidothioate, O-methyl-S-phenyl-phenylpropylphosphoramidothioate, S-methyl-1,2,3-benzothiadiazole-7-carbothioate, spiro[2H]-1-benzopyran-2,1'(3'H)-isobenzofiaran]-3'-one, Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalarn, copper sulfate and other copper preparations.

Insecticides/Acaricides/Nematicides:

abarnectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, Baculoviren, *Beauveria bassiana, Beauveria tenella*, bendiocarb, benfuracarb, bensultap, benzoximate, betacyfluthrin, bifenazate, bifenthrin, bioethanomethrin, bioperrnethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathi on, ivermectin, nuclear polyhedrosis viruses, lambda-cyhalothrin, lufenuron, malathion, mecarbam, metaldehyde, methamidophos, Metharhizium anisopliae, Metharhizium flaviviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pynproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypernethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, verticillium lecanii,

YI 5302, zeta-cypermnethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)-methyl]tetrahydro-3,5-dimethyl-N-nitro-1,3,5-triazine-2(1H)-imine, 2-(2-chloro-6-fluorophenyl)-4-[4-(1,1-dimethylethyl)-phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]1-fluoro-2-phenoxy-benzene, 4-chloro-2-(1,1-dimethylethyl)-5-[[2-(2,6-dimethyl-4-phenoxyphenoxy)ethyl]thio]3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)-methoxy]-2-(3,4-dichlorophenyl)-3(2H)-pyridazinone, Bacillus thuringiensis strain EG-2348, 2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl-[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)-methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl-[2-(dipropylamino)-2-oxoethyl]-ethylphosphoramidothioate.

A mixture with other known active compounds, such as herbicides, or with fertilizers and growth regulators, is also possible.

The active compounds can be used as such, in the form of their formulations or the use forms prepared therefrom, such as ready-to-use solutions, suspensions, wettable powders, pastes, soluble powders, dusting agents and granules. They are used in a customary manner, for example by pouring, spraying, atomizing, broadcasting, dusting, foam application, brushing, etc. It is also possible to apply the active compounds by the Ultra-Low-Volume method or to inject the active compound formulation or the active compound itself into the soil. The seed of the plants may also be treated.

When the active compounds according to the invention are used as fungicides, the application rates may be varied within a relatively large range, depending on the method of application. In the treatment of plant parts, the application rates of active compound are in general between 0.1 and 10,000 g/ha, preferably between 10 and 1000 g/ha. In the treatment of seed, the application rates of active compound are in general between 0.001 and 50 g per kilogram of seed, preferably between 0.01 and 10 g per kilogram of seed. In the treatment of the soil, the application rates of active compound are in general between 0.1 and 10,000 g/ha, preferably between 1 and 5000 g/ha.

The compositions used for protecting technical materials contain the active compounds in general in an amount of 1 to 95%, preferably of 10 to 75%.

The use concentrations of the active compounds according to the invention depend on the type and occurrence of the microorganisms to be controlled and on the composition of the material to be protected. The optimal amount for use can be determined by test series. In general, the use concentrations are in the range from 0.001 to 5% by weight, preferably from 0.05 to 1.0% by weight, based on the material to be protected.

The activity and the action spectrum of the active compounds to be used according to the invention in material protection or of the compositions, concentrates or very generally formulations which can be prepared therefrom can be increased if optionally further antimicrobial compounds, fungicides, bactericides, herbicides, insecticides or other active compounds are added for increasing the action spectrum or achieving special effects, such as, for example, additional protection from insects. These mixtures may have a broader action spectrum than the compounds according to the invention.

Even when used against animal pests, the compounds according to the invention may be present as a mixture with synergistic agents in commercial formulations and in the use forms prepared from these formulations. Synergistic agents are compounds by means of which the action of the active compounds is increased without the added synergistic agent itself having to be actively effective.

The active compound content of the use forms prepared from the commercial formulations may vary within wide ranges. The active compound concentration of the use forms may be from 0.0000001 to 95% by weight of active compound, preferably between 0.0001 and 1% by weight.

Application is effected in a customary manner adapted to the use forms.

The preparation and use of compounds according to the invention are illustrated by the following examples.

PREPARATION EXAMPLES

Example 1

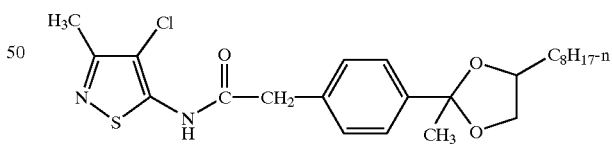

A mixture of 0.9 g (2.2 mmol) of 5-[(4-acetyl-phenyl)-acetylamino]-4-chloro-3-methyl-isothiazole, 0.35 g (2.6 mmol) of 1,2-decanediol, 10 mg of toluenesulfonic acid, 2.0 g of molecular sieves (3A) and 15 ml of toluene is heated under reflux for 18 hours. After cooling to room temperature, the reaction mixture is washed successively with water and saturated aqueous sodium bicarbonate solution. The organic phase is concentrated under reduced pressure. This gives 0.92 g (90% of theory) of a solid consisting of the two isomers of the compound of the formula given above in a ratio of 60:40.

log p (pH 2.3)=5.84 and 6.05.

Preparation of the Starting Material

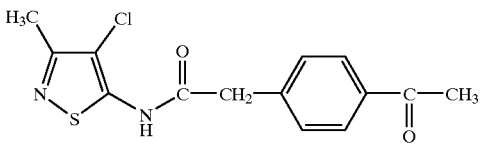

At room temperature, 8.4 g (47.1 mmol) of 4-acetyl-phenylacetic acid and 10.1 g (47.1 mmol) of dicyclohexyl-carbodiimide are added successively with stirring to a mixture of 7.0 g (47.1 mmol) of 5-amino-4-chloro-3-methyl-isothiazole and 150 ml of methylene chloride. The reaction mixture is stirred at room temperature for 18 hours. The precipitated solid is then filtered off with suction and the filtrate is concentrated under reduced pressure. The product that remains is chromatographed on silica gel using the mobile phase cyclohexane/ethyl acetate=1:1. Concentration of the eluate gives 11.8 g (81% of theory) of 5-[(4-acetylphenyl)-acetylamino]-4-chloro-3-methyl-isothiazole in the form of a solid.

log p (pH 2.3)=2.12.

The phenylacetic acid heterocyclyl amides of the formula (I) listed in Table 13 below are likewise prepared by the methods given above.

TABLE 13

Structure (In): $R^1$-substituted thiadiazole with X linker, connected via NH-C(O)-CH$_2$-phenyl-C($R^3$)(dioxane ring with O-A-O and $R^4_n$ substituent)

| Example No. | $R^1$ | X | $R^3$/dioxolane substituent | log p (acidic)(*) |
|---|---|---|---|---|
| 2 | CH$_3$ | CH | 2,2-dimethyl-1,3-dioxolane-4-yl-CH$_2$-O-CH$_2$-CH=CH$_2$ | 2.33 |
| 3 | CH$_3$ | CCl | 2,2-dimethyl-4-phenyl-1,3-dioxolane | 3.83 |
| 4 | CH$_3$ | CCl | 2,2-dimethyl-1,3-dioxolane-4-yl-CH$_2$-O-CH$_2$-CH=CH$_2$ | 3.23 |
| 5 | CH$_3$ | CCl | 2,2-dimethyl-1,3-dioxolane-4-yl-C(CH$_3$)$_3$ | 4.00 |
| 6 | CH$_3$ | CCl | 2,2-dimethyl-1,3-dioxolane-4-yl-CH$_2$Cl | 3.09 |
| 7 | CH$_3$ | CCl | 2,2-dimethyl-1,3-dioxolane-4-yl-C$_2$H$_5$ | 3.23 |
| 8 | CH$_3$ | CCl | 2,2-dimethyl-1,3-dioxolane-4-yl-(CH$_2$)$_3$-CH=CH-CH$_3$ | 4.40 |

TABLE 13-continued (In)

[Structure: R¹-substituted thiadiazole-NH-C(=O)-CH₂-phenyl-C(R³)(O-A)(O)-CH₂-CR⁴ₙ dioxane system]

| Example No. | R¹ | X | [R³/A/R⁴ₙ structure] | log p (acidic)(*) |
|---|---|---|---|---|
| 9 | CH₃ | CCl | 2,2-dimethyl-1,3-dioxolan-4-yl-CH₂-O-(4-chlorophenyl) | 4.24 |
| 10 | CH₃ | CCl | 2,2-dimethyl-5-phenyl-1,3-dioxane | 3.79 |
| 11 | CH₃ | CCl | 3,3-dimethyl-2,4-dioxaspiro[5.5]undec-8-ene, 9-Cl | 4.26 |
| 12 | CH₃ | CCl | 3,3-dimethyl-2,4,8,10-tetraoxaspiro[5.5]undecane | 2.59 |
| 13 | CH₃ | CCl | 2,2-dimethyl-4-C₉H₁₉-1,3-dioxolane | 5.89 |
| 14 | CH₃ | CCl | 2,2-dimethyl-4-(2,3-dichlorophenyl)-1,3-dioxolane | 4.84 |
| 15 | CH₃ | CCl | 2,2-dimethyl-4-(3-chlorophenyl)-1,3-dioxolane | 4.32 |
| 16 | CH₃ | CCl | 2,2-dimethyl-4-(3,4-dichlorophenyl)-1,3-dioxolane | 4.82 |

TABLE 13-continued
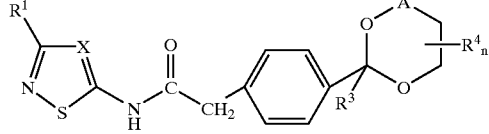
(In)
| Example No. | R¹ | X | [structure] | log p (acidic)(*) |
|---|---|---|---|---|
| 17 | CH₃ | CCl | 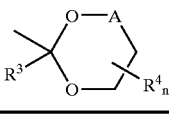 | 4.35 |
| 18 | CH₃ | CCl | 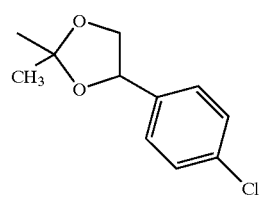 | 2.80 |
| 19 | CH₃ | CCl | 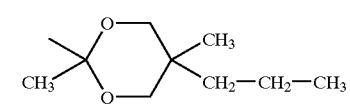 | 3.91 |
| 20 | CH₃ | CCl | 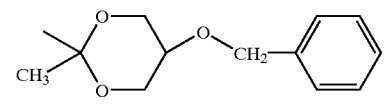 | 4.21 |
| 21 | CH₃ | CCl | 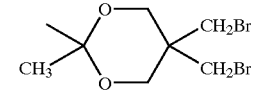 | 3.97 |
(*)In all cases, isomer mixtures are present. What is stated is in each case the higher log p value.
TABLE 14
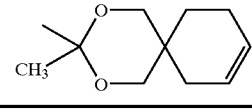
(Ip)
| Example No. | R¹ | X | [structure] | log p (acidic)(*) |
|---|---|---|---|---|
| 22 | CH₃ | N | 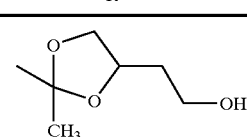 | 1.59 |

TABLE 14-continued (Ip)

| No. | R¹ | X | R³ structure | log p (acidic)(*) |
|-----|-----|---|---|---|
| 23 | CH₃ | N | dioxolane with CH₃, CH₃ and CH₂-O-butyl | 3.16 |
| 24 | CH₃ | N | dioxolane with CH₃, CH₃ and t-butyl | 3.35 |
| 25 | CH₃ | N | dioxolane with CH₃, CH₃ and propyl | 2.99 |
| 26 | ethyl | N | dioxolane with CH₃, CH₃ and ethyl | 2.96 |
| 27 | ethyl | N | dioxolane with CH₃, CH₃ and CH₂CH₂OH | 2.81 |
| 28 | ethyl | N | dioxolane with CH₃, CH₃ and t-butyl | 3.78 |

(*)In all cases, isomer mixtures are present. What is stated is in each case the higher log p value.

Preparation of Starting Materials

Example 29

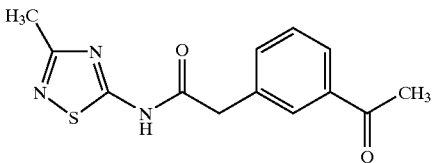

At room temperature, 7.9 g (40 mmol) of 3,-acetylphenylacetyl chloride in 20 ml of dichloromethane are added with stirring to a mixture of 4.6 g (40 mmol) of 5-amino-3-methyl-1,2,4-thiadiazole and 12.8 g (162 mmol) of pyridine in 50 ml of dichloromethane. The reaction mixture is stirred at room temperature for 16 hours, admixed with 20 mg of 4-dimethylaminopyridine and stirred at room temperature for a further 24 hours. The reaction solution is then washed with 1N-HCl, dried over sodium sulfate and concentrated under reduced pressure. Titration of the resulting residue with diethyl ether gives 5.5 g (50% of theory) of 5-[3(-acetylphenyl)acetaminol]-3-methyl-1,2,4-thiadiazole in the form of a solid.

m.p. 91–98° C.; log P (pH 2.3)=1.56.

Example 30

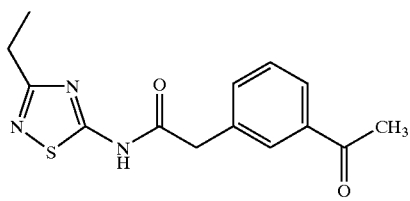

At from 0° to 10° C., 15.7 g (80 mmol) of 3-acetylphenylacetyl chloride in 40 ml of dichloromethane are added with stirring to a mixture of 10.3 g (80 mmol) of 5-amino-3-ethyl-1,2,4-thiadiazole, 25.6 g (324 mmol) of pyridine and 40 mg of 4-dimethylaminopyridine in 100 ml of dichloromethane. The reaction mixture is stirred at room temperature for 16 hours and then washed with 1N-HCl, dried over sodium sulfate and concentrated under reduced pressure. Titration of the resulting residue with diethyl ether gives 15.8 g (68.4% of theory) of 5-[3-acetylphenyl)-acetamino]-3-ethyl-1,2,4-thiadiazole in the form of a solid.

m.p. 121–125° C.; log P (pH 2.3)=1.87.

Example 31

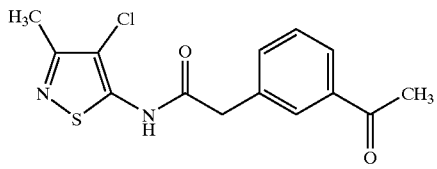

At from 0° to 10° C., 15.7 g (80 mmol) of 3-acetylphenylacetyl chloride in 40 ml of dichloromethane are added with stirring to a mixture of 11.9 g (80 mmol) of 5-amino-4-chloro-3-methyl-isothiazole, 25.6 g (324 mmol) of pyridine and 40 mg of 4-dimethylaminopyridine in 100 ml of dichloromethane. The reaction mixture is stirred at room temperature for 16 hours and then washed with 1N-HCl, dried over sodium sulfate and concentrated under reduced pressure. Titration of the resulting residue with diethyl ether gives 16.9 g (69% of theory) of 5-[3-(acetylphenyl)-acetaminol]-4-chloro-3-methyl-isothiazole in the form of a solid.

m.p. 77–83° C.; log P (pH 2.3)=2.14.

Use Examples

Example A

Plasmopara Test (Grapevine)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for the protective activity, young plants are sprayed with the preparation of active compound at the stated application rate. After the spray coating has dried on, the plants are inoculated with an aqueous spore suspension of *Plasmopara vilicola* and then remain in an incubation cabin at about 20° C. and 100% relative atmospheric humidity for 1 day. The plants are then placed in a greenhouse at about 21° C. and about 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

Active compounds, application rates and test results are shown in the table below.

TABLE A

| Plasmopara test (grapevine) / protective | | |
|---|---|---|
| Active compound | Application rate of active compound in g/ha | Efficacy in % |
| According to the invention: | | |
| (3) ![structure] | 100 | 99 |
| (4) ![structure] | 100 | 100 |

TABLE A-continued

Plasmopara test (grapevine) / protective

| Active compound | Application rate of active compound in g/ha | Efficacy in % |
|---|---|---|
| (6) isothiazole-NHC(O)CH$_2$-C$_6$H$_4$-[dioxolane with CH$_3$ and CH$_2$Cl] | 100 | 100 |
| (7) isothiazole-NHC(O)CH$_2$-C$_6$H$_4$-[dioxolane with CH$_3$ and C$_2$H$_5$] | 100 | 100 |
| (8) isothiazole-NHC(O)CH$_2$-C$_6$H$_4$-[dioxolane with CH$_3$ and (CH$_2$)$_3$·CH=CH=CH$_3$] | 100 | 97 |
| (9) isothiazole-NHC(O)CH$_2$-C$_6$H$_4$-[dioxolane with CH$_3$ and CH$_2$-O-C$_6$H$_4$-Cl] | 100 | 100 |
| (10) isothiazole-NHC(O)CH$_2$-C$_6$H$_4$-[dioxane with CH$_3$ and phenyl] | 100 | 99 |
| (15) isothiazole-NHC(O)CH$_2$-C$_6$H$_4$-[dioxolane with CH$_3$ and 3-Cl-C$_6$H$_4$] | 100 | 97 |
| (17) isothiazole-NHC(O)CH$_2$-C$_6$H$_4$-[dioxolane with CH$_3$ and 4-Cl-C$_6$H$_4$] | 100 | 97 |
| (18) isothiazole-NHC(O)CH$_2$-C$_6$H$_4$-[dioxane with CH$_3$, CH$_3$ and C$_3$H$_7$-n] | 100 | 99 |

In each structure, the isothiazole moiety is 4-chloro-3-methyl-isothiazol-5-yl.

TABLE A-continued

Plasmopara test (grapevine) / protective

| Active compound | Application rate of active compound in g/ha | Efficacy in % |
|---|---|---|
|  (20) | 100 | 96 |

Example B

Podosphaera Test (Apple)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the causative organism of apple mildew *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE B

Podosphaera test (apple) / protective

| Active compound | Application rate of active compound in g/ha | Efficacy in % |
|---|---|---|
| According to the invention: | | |
| (3) | 100 | 99 |
| (7) | 100 | 97 |
| (8) | 100 | 95 |

TABLE B-continued

Podosphaera test (apple) / protective

| Active compound | Application rate of active compound in g/ha | Efficacy in % |
|---|---|---|
| (9) 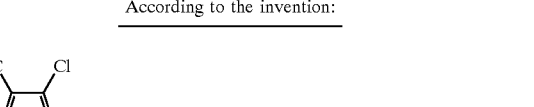 | 100 | 97 |
| (17) 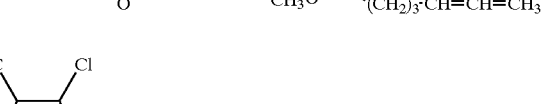 | 100 | 99 |

Example C

Erysiphe Test (Wheat)/Protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores von *Erysiphe graminis* f.sp. *tritici*.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE C

Erysiphe test (wheat) / protective

| Active compound | Application rate of active compound in g/ha | Efficacy in % |
|---|---|---|
| *According to the invention:* | | |
| (8) | 500 | 81 |
| (7) | 1000 | 81 |

TABLE C-continued

Erysiphe test (wheat) / protective

| Active compound | Application rate of active compound in g/ha | Efficacy in % |
|---|---|---|
| (10) isothiazole-NH-C(=O)-CH₂-C₆H₄-C(CH₃)(O-CH₂-CH(-)-O-)-CH₂-O-C₆H₄-Cl (3-methyl-4-chloro-isothiazol-5-yl amide with 1,3-dioxolane bearing 4-chlorophenoxymethyl) | 500 | 81 |

Example D

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are populated with larvae of the green rice leafhopper (*Nephotettix cincticeps*) while the seedlings are still moist.

After the desired period of time, the kill in % is determined. 100% means that all leaf hoppers have been killed; 0% means that none of the leaf hoppers have been killed.

Active compounds, application rates and test results are shown in the table below.

TABLE D

Plant-damaging insects
Nephotettix test

| Active compound | Concentration of active compound in % | Kill rate in % after 6ᵈ |
|---|---|---|
| (5) according to the invention — 3-methyl-4-chloro-isothiazol-5-yl amide of phenylacetic acid with 1,3-dioxolane bearing CH₃ and C(CH₃)₃ | 0.1 | 100 |
| (20) according to the invention — 3-methyl-4-chloro-isothiazol-5-yl amide of phenylacetic acid with 1,3-dioxane bearing CH₃ and C(CH₂Br)₂ | 0.1 | 100 |
| (6) according to the invention — 3-methyl-4-chloro-isothiazol-5-yl amide of phenylacetic acid with 1,3-dioxolane bearing CH₃ and CH₂Cl | 0.1 | 100 |

TABLE D-continued

Plant-damaging insects
Nephotettix test

| Active compound | Concentration of active compound in % | Kill rate in % after 6$^d$ |
|---|---|---|
| 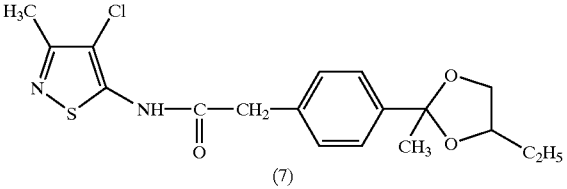(7) according to the invention | 0.1 | 100 |

Example E

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

Active compounds, application rates and test results are shown in the table below.

TABLE E

Plant-damaging insects
Phaedon larvae test

| Active compound | Concentration of active compound in % | Kill rate in % after 7$^d$ |
|---|---|---|
| 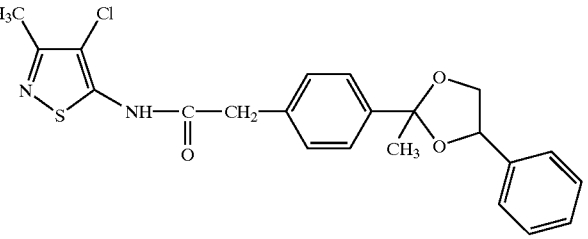(3) according to the invention | 0.1 | 100 |
| 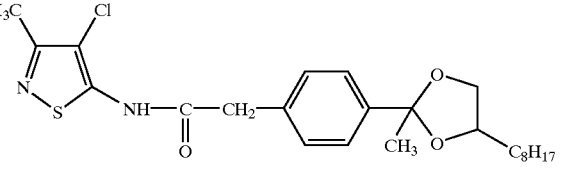(1) according to the invention | 0.1 | 100 |
| 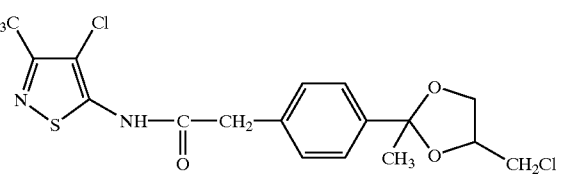 | 0.1 | 100 |

TABLE E-continued
Plant-damaging insects
Phaedon larvae test
| Active compound | Concentration of active compound in % | Kill rate in % after 7$^d$ |
|---|---|---|
(6)
according to the invention
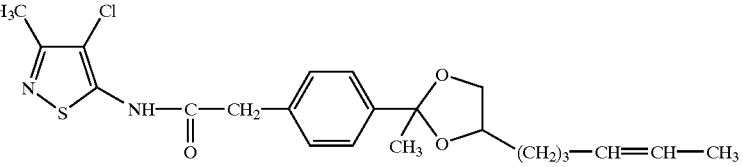
0.1　　100
(8)
according to the invention
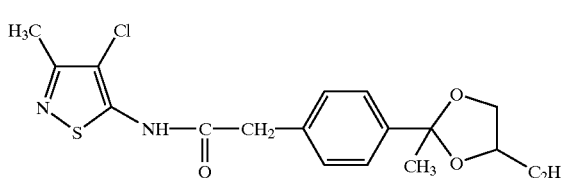
0.1　　100
(7)
according to the invention
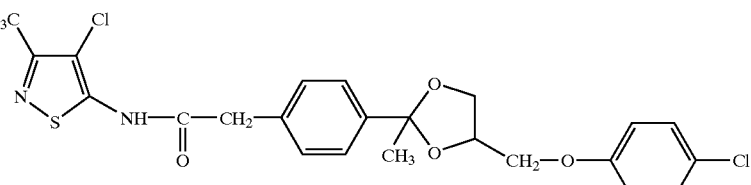
0.1　　100
(9)
according to the invention
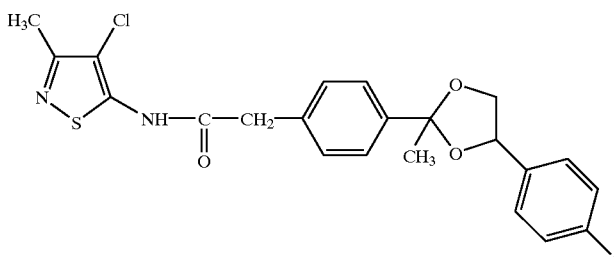
0.1　　100
(17)
according to the invention
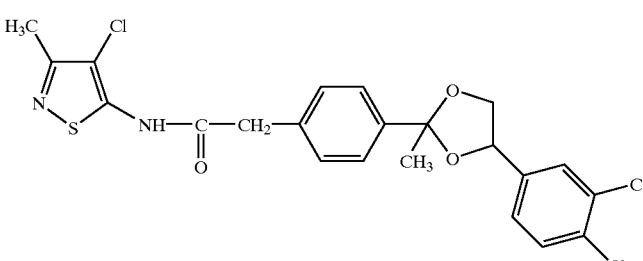
0.1　　100
(16)
according to the invention
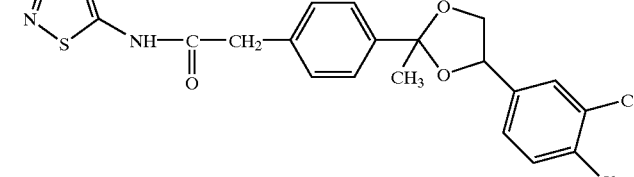

Example F

Spodoptera Frugiperda Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the army worm *Spodoptera frugiperda* while the leaves are still moist.

After the desired period of time, the effect in % is determined. 100% means that all caterpillars have been killed; 0% means that none of the caterpillars have been killed.

Active compounds, application rates and test results are shown in the table below.

TABLE F

Plant-damaging insects
*Spodoptera frugiperda* test

| Active compound | Concentration of active compound in % | Kill rate in % after $7^d$ |
|---|---|---|
| 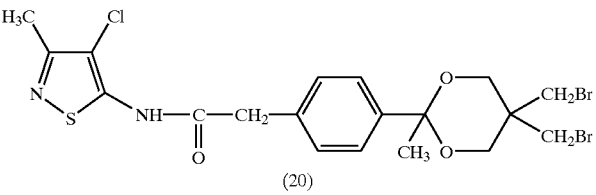<br>(20) according to the invention | 0.1 | 100 |
| 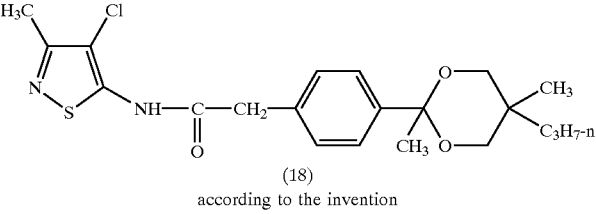<br>(18) according to the invention | 0.1 | 100 |
| 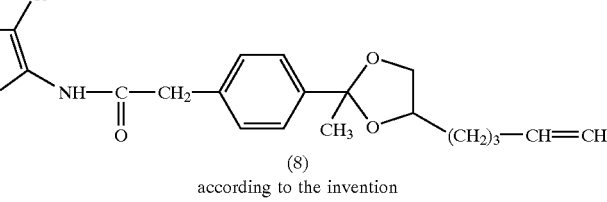<br>(8) according to the invention | 0.1 | 100 |
| 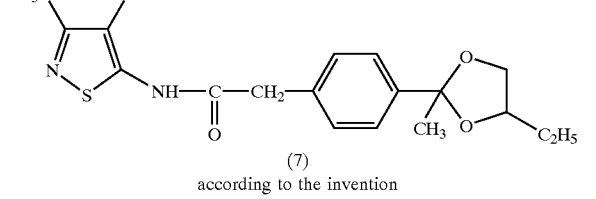<br>(7) according to the invention | 0.1 | 100 |
| 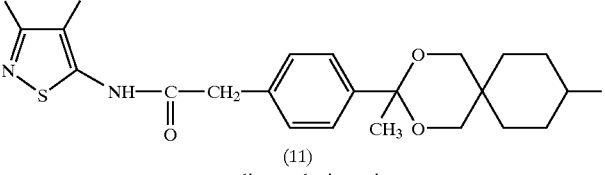<br>(11) according to the invention | 0.1 | 100 |

TABLE F-continued

Plant-damaging insects
Spodoptera frugiperda test

| Active compound | Concentration of active compound in % | Kill rate in % after 7$^d$ |
|---|---|---|
| (17) according to the invention [structure: 4-chloro-3-methylisothiazol-5-yl-NH-C(=O)-CH$_2$-C$_6$H$_4$-C(CH$_3$)(O-CH$_2$-CH(O-)-C$_6$H$_4$-Cl)] | 0.1 | 100 |

Example G

Tetranychus Test (OP-resistant/dip Treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

Active compounds, application rates and test results are shown in the table below.

TABLE G

Plant-damaging insects
Tetranychus test (OP-resistant/dip treatment)

| Active compound | Concentration of active compound in % | Kill rate in % after 7$^d$ |
|---|---|---|
| (5) according to the invention [structure with C(CH$_3$)$_3$ group] | 0.01 | 100 |
| (4) according to the invention [structure with O-CH$_2$-CH=CH$_2$ (allyloxy) group] | 0.01 | 100 |

TABLE G-continued

Plant-damaging insects
Tetranychus test (OP-resistant/dip treatment)

| Active compound | Concentration of active compound in % | Kill rate in % after 7$^d$ |
|---|---|---|

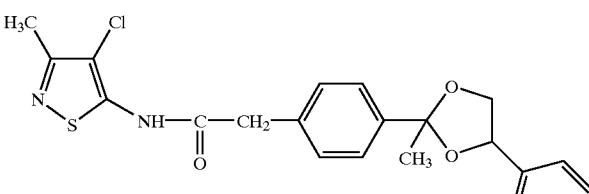

(3)
according to the invention 0.01   100

(8)
according to the invention 0.01   100

What is claimed:

1. A phenylacetic acid heterocyclyl amide of the formula

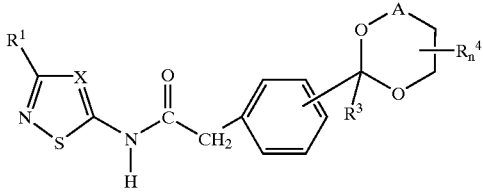

(I)

wherein

R$^1$ represents alkyl, halogenoalkyl, alkoxyalkyl, alkylthioalkyl, alkoxy, alkylthio or represents optionally substituted cycloalkyl, R$^2$ represents hydrogen, alkylcarbonyl, alkoxycarbonyl or represents in each case optionally substituted arylcarbonyl, aryloxycarbonyl or aralkyloxycarbonyl, R$^3$ represents hydrogen or alkyl, R$^4$ represents optionally substituted alkyl, optionally substituted alkenyl, optionally substituted alkinyl, optionally substituted aryl, optionally substituted aralkyl, optionally substituted aralkyloxy or represents optionally substituted aralkyloxyalkyl, or two geminal or vicinal R$^4$ radicals together with the carbon atom(s) to which they are attached form a saturated or unsaturated, optionally substituted five- or six-membered ring which may contain one or two hetero atoms, n represents integers from 1 to 4, X represents a nitrogen atom or represents a grouping of the formula CH, CCl, CBr, C—CN, C—C≡CH or

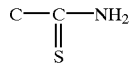

and

A represents a direct bond or a CH$_2$ group.

2. A process for preparing a phenylacetic acid heterocyclyl amide of the formula (I) according to claim 1, comprising the step of reacting an amino derivative of the formula

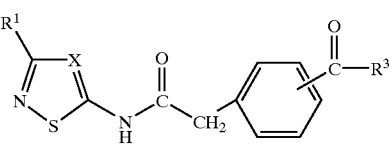

(II)

wherein

R$^1$, R$^3$ and X are as defined in claim 1, with a diol of the formula

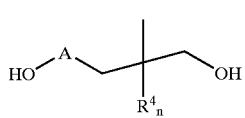

(III)

wherein

A, R$^4$ and n are as defined in claim 1, to obtain a phenylacetic acid heterocyclyl amide of the formula

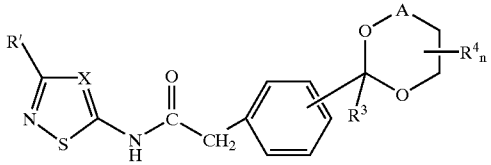

(Ia)

wherein

R¹, R³, R⁴, A, X and n are as defined in claim 1.

3. A process for preparing a phenylacetic acid heterocyclyl amide of the formula (I) according to claim 1, comprising the step of reacting the phenylacetic acid heterocyclyl amide of the formula

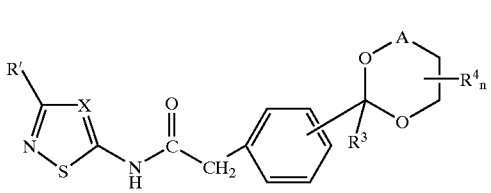

(Ia)

wherein

R¹, R³, R⁴, A, X and n are as defined in claim 1, with an acid halide of the formula

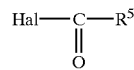

(IV)

wherein

Hal represents chlorine or bromine and

R⁵ represents alkyl, alkoxy or represents in each case optionally substituted aryl, aryloxy or aralkyloxy, in the presence of a diluent and in the presence of an acid binder.

4. A composition for controlling undesirable microorganisms and animal pests, comprising one or more phenylacetic acid heterocyclyl amides of the formula (I) according to claim 1, and an ingredient selected from the group consisting of extenders, surfactants and mixtures thereof.

5. A method for controlling undesirable microorganisms and animal pests, comprising the step of applying one or more phenylacetic acid heterocyclyl amides of the formula (I) according to claim 1, to the undesirable microorganisms or animal pests and/or their habitat.

6. An amino derivative of the formula

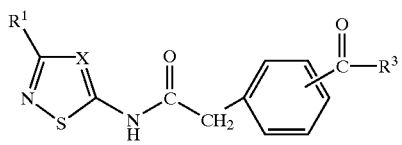

(II)

wherein

R¹ represents alkyl, halogenoalkyl, alkoxyalkyl, alkylthioalkyl, alkoxy, alkylthio or represents optionally substituted cycloalkyl, R³ represents hydrogen or alkyl and X represents a nitrogen atom or represents a grouping of the formula CH, C—Cl, C—Br, C—CN, C—C≡CH or

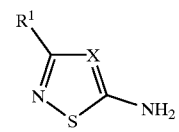

7. A process for preparing amino derivatives of the formula (II) according to claim 6, comprising the step of:
c) reacting a heterocyclyl-amine of the formula

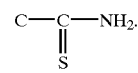

(V)

wherein

R¹ and X are as defined in claim 6, with either

α) an acid halide of the formula

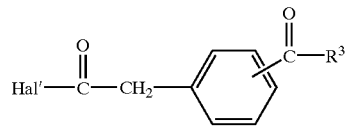

(VI)

wherein

R³ is as defined in claim 6 and

Hal¹ represents chlorine or bromine, or

β) a phenylacetic acid derivative of the formula

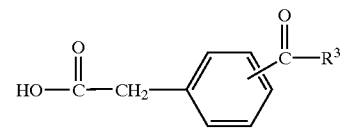

(VII)

wherein

R³ is as defined in claim 6, in the presence of a catalyst and in the presence of a diluent.

8. A phenylacetic acid heterocyclyl amide according to claim 1, having the formula

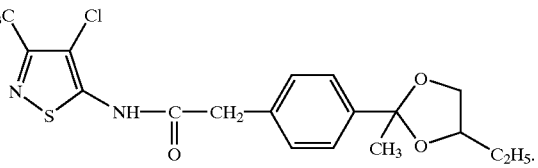

9. A phenylacetic acid heterocyclyl amide according to claim 1, having the formula

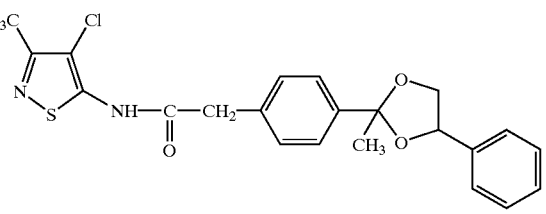

10. A phenylacetic acid heterocyclyl amide according to claim 1, wherein $R^1$ represents $C_1$–$C_4$-alkyl, $C_1$–$C_4$-halogenoalkyl having 1 to 5 fluorine, chlorine and/or bromine atoms, or represents $C_1$–$C_4$-alkoxy-$C_1$–$C_4$-alkyl, $C_1$–$C_4$-alkylthio-$C_1$–$C_4$-alkyl, $C_1$–$C_4$-alkoxy, $C_1$–$C_4$-alkylthio or represents $C_3$–$C_6$-cycloalkyl which is unsubstituted or mono- to trisubstituted by identical or different substituents from the group consisting of $C_1$–$C_4$-alkyl and halogen, $R^2$ represents hydrogen, $C_1$–$C_4$-alkyl-carbonyl, $C_1$–$C_4$-alkoxy-carbonyl or represents phenyl-carbonyl, phenyloxy-carbonyl or phenyl-$C_1$–$C_4$-alkyloxycarbonyl, where the three last mentioned radicals may be unsubstituted or mono- to trisubstituted in the phenyl moiety by identical or different substituents from the group consisting of halogen, nitro, cyano, $C_1$–$C_4$-alkyl, $C_1$–$C_4$-alkoxy, $C_1$–$C_4$-alkylthio, halogenoalkyl having 1 or 2 carbon atoms and 1 to 5 identical or different halogen atoms, halogenoalkoxy having 1 or 2 carbon atoms and 1 to 5 identical or different halogen atoms and/or halogenoalkylthio having 1 or 2 carbon atoms and 1 to 5 identical or different halogen atoms, $R^3$ represents hydrogen or $C_1$–$C_4$-alkyl, and $R^4$ represents $C_1$–$C_{12}$-alkyl, $C_1$–$C_8$-halogenoalkyl having 1 to 8 identical or different halogen atoms, $C_1$–$C_4$-hydroxyalkyl, $C_2$–$C_8$-halogenoalkenyl having 1 to 8 identical or different halogen atoms, $C_2$–$C_8$-alkinyl, $C_2$–$C_8$-halogenoalkinyl having 1 to 8 halogen atoms, $C_1$–$C_8$-alkoxy-$C_1$–$C_4$-alkyl, $C_2$–$C_8$-alkenoxy-$C_1$–$C_4$-alkyl, $C_2$–$C_8$-alkinoxy-$C_1$–$C_4$-alkyl, $C_1$–$C_8$-halogenoalkoxy-$C_1$–$C_4$-alkyl having 1 to 8 identical or different halogen atoms, $C_2$–$C_8$-halogenoalkenyloxy-$C_1$–$C_4$-alkyl having 1 to 8 identical or different halogen atoms, $C_2$–$C_8$-halogenoalkinyloxy-$C_1$–$C_4$-alkyl having 1 to 8 identical or different halogen atoms, $C_1$–$C_8$-alkoxycarbonyl-$C_1$–$C_4$-alkyl, $C_1$–$C_8$-alkylcarbonyloxy-$C_1$–$C_4$alkyl, $C_1$–$C_8$-halogenoalkylcarbonyloxy-$C_1$–$C_4$-alkyl having 1 to 8 identical or different halogen atoms, $C_1$–$C_8$-alkylthio-$C_1$–$C_4$-alkyl, or represents phenyl, phenylalkyl having 1 to 4 carbon atoms in the alkyl moiety, phenylalkoxy having 1 to 4 carbon atoms in the alkoxy moiety or represents phenylalkyloxyalkyl having 1 to 4 carbon atoms in the alkyl moiety and 1 to 4 carbon atoms in the oxyalkyl moiety, where the four last mentioned radicals may be unsubstituted or mono- to trisubstituted in the phenyl moiety by identical or different substituents from the group consisting of halogen, nitro, cyano, $C_1$–$C_4$-alkyl, $C_1$–$C_4$-alkoxy, $C_1$–$C_4$-alkylthio, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, alkylsulfinyl having 1 to 4 carbon atoms, alkylsulfonyl having 1 to 4 carbon atoms, alkylcarbonyl having 1 to 4 carbon atoms in the alkyl moiety and alkoxycarbonyl having 1 to 4 carbon atoms in the alkoxy moiety, or two geminal or vicinal $R^4$ radicals together with the carbon atoms to which they are attached represent a saturated or unsaturated five- or six-membered ring which may contain one or two oxygen, sulfur and/or nitrogen atoms and which may be unsubstituted or mono- or disubstituted by halogen, alkyl having 1 to 4 carbon atoms and/or alkoxy having 1 to 4 carbon atoms.

11. A phenylacetic acid heterocyclyl amide according to claims 10, wherein n represents 1, 2 or 3.

12. A phenylacetic acid heterocyclyl amide according to claim 10, wherein $R^1$ represents methyl, ethyl, propyl, isopropyl, n-butyl, i-butyl, sec-butyl, tert-butyl, halogenoalkyl having 1 or 2 carbon atoms and 1 to 3 fluorine, chlorine, and/or bromine atoms, alkoxyalkyl having 1 or 2 carbon atoms in the alkoxy moiety and 1 or 2 carbon atoms in the alkyl moiety, alkylthioalkyl having 1 or 2 carbon atoms in the alkylthio moiety and 1 or 2 carbon atoms in the alkyl moiety, methoxy, ethoxy, methylthio, ethylthio or represents cyclopentyl, cyclohexyl or cyclopropyl, optionally mono- or disubstituted by methyl, ethyl, fluorine and/or chlorine, $R^2$ represents hydrogen, methylcarbonyl, ethylcarbonyl, methoxycarbonyl, ethoxycarbonyl, propoxycarbonyl, isopropoxycarbonyl, butoxycarbonyl, i-butoxycarbonyl, sec-butoxycarbonyl, tert-butoxycarbonyl, phenylcarbonyl, phenyloxycarbonyl or phenylalkoxycarbonyl having 1 or 2 carbon atoms in the alkoxy moiety, where the three last mentioned radicals may be mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy and trifluoromethylthio, $R^3$ represents hydrogen, methyl or ethyl, and $R^4$ represents $C_1$–$C_{10}$-alkyl, halogenoalkyl having 1 to 8 carbon atoms and 1 to 8 fluorine, chlorine and/or bromine atoms, hydroxyalkyl having 1 or 2 carbon atoms, $C_2$–$C_8$-alkenyl, $C_2$–$C_8$-halogenoalkenyl having 1 to 8 fluorine, chlorine and/or bromine atoms, $C_2$–$C_8$-alkinyl, $C_2$–$C_8$-halogenoalkinyl having 1 to 8 fluorine, chlorine and/or bromine atoms, $C_1$–$C_8$-alkoxy-$C_1$–$C_2$-alkyl, $C_2$–$C_8$-alkenoxy-$C_1$–$C_2$-alkyl, $C_2$–$C_8$-alkinoxy-$C_1$–$C_2$-alkyl, $C_1$–$C_6$-halogenoalkoxy-$C_1$–$C_2$-alkyl having 1 to 5 fluorine, chlorine and/or bromine atoms, $C_2$–$C_6$halogenoalkenyloxy-$C_1$–$C_2$-alkyl having 1 to 5 fluorine, chlorine and/or bromine atoms, $C_2$–$C_6$-halogenoalkinyloxy-$C_1$–$C_2$-alkyl having 1 to 5 fluorine, chlorine and/or bromine atoms, $C_1$–$C_8$-alkoxy-carbonyl-$C_1$–$C_2$-alkyl, $C_1$–$C_8$-alkylcarbonyloxy-$C_1$–$C_2$-alkyl, $C_1$–$C_6$-halogenoalkylcarbonyloxy-$C_1$–$C_2$-alkyl having 1 to 5 fluorine, chlorine and/or bromine atoms, $C_1$–$C_6$-alkylthio-$C_1$–$C_2$-alkyl or represents phenyl, phenylalkyl having 1 or 2 carbon atoms in the alkyl moiety, phenylalkoxy having 1 or 2 carbon atoms in the alkoxy moiety or represents phenylalkyl-oxyalkyl having 1 or 2 carbon atoms in the alkyl moiety and 1 or 2 carbon atoms in the oxyalkyl moiety, where the four last mentioned radicals may be mono- to trisubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy, trifluoromethylthio, methylsulfinyl, methylsulfonyl, methylcarbonyl, ethylcarbonyl, methoxycarbonyl and/or ethoxycarbonyl, or two geminal or vicinal $R^4$ radicals together with the carbon atoms to which they are represent a saturated or monounsaturated six-membered ring which may contain one or two oxygen, sulfur and/or nitrogen atoms and which may be mono- or disubstituted by fluorine, chlorine, methyl, ethyl and/or methoxy.

13. A phenylacetic acid heterocyclyl amide according to claim 12, wherein n represents 1 or 2.

14. A phenylacetic acid heterocyclyl amide of the formula

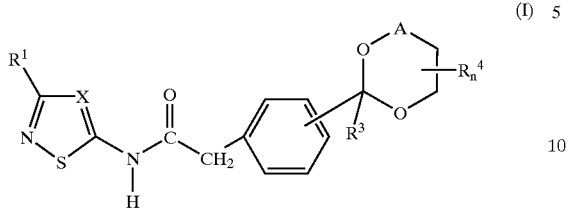

(I)

wherein
- $R^1$ represents methyl, ethyl, chloromethyl, difluoromethyl, trifluoromethyl, methoxymethyl, ethoxymethyl, methylthiomethyl, methoxy, ethoxy, methylthio, cyclopropyl, cyclopentyl or cyclohexyl,
- $R^2$ represents hydrogen, methylcarbonyl, ethylcarbonyl, methoxycarbonyl, ethoxycarbonyl, phenylcarbonyl, phenyloxycarbonyl or phenylmethoxycarbonyl, where the three last mentioned radicals may be unsubstituted or mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy and trifluoromethylthio,
- $R^3$ represents hydrogen or methyl,
- $R^4$ represents $C_1$–$C_{10}$-alkyl, halogenoalkyl having 1 to 4 carbon atoms and 1 to 5 fluorine, chlorine and/or bromine atoms, hydroxymethyl, hydroxyethyl, $C_2$–$C_6$-alkenyl, $C_2$–$C_6$-halogenoalkenyl having 1 to 5 fluorine, chlorine and/or bromine atoms, $C_2$–$C_6$-alkinyl, $C_2$–$C_6$-halogenoalkinyl having 1 to 5 fluorine, chlorine and/or bromine atoms, $C_1$–$C_6$-alkoxy-methyl, $C_2$–$C_6$-alkenoxy-methyl, $C_2$–$C_6$-alkinoxy-methyl, $C_1$–$C_4$-halogenoalkoxy-methyl having 1 to 3 fluorine, chlorine and/or bromine atoms, $C_2$–$C_4$-halogenoalkenyloxy-methyl having 1 to 3 fluorine, chlorine and/or bromine atoms, $C_2$–$C_4$-halogenoalkinyloxy-methyl having 1 to 3 fluorine, chlorine and/or bromine atoms, $C_1$–$C_4$-alkoxy-carbonyl-methyl, $C_1$–$C_4$-alkyl-carbonyloxy-methyl, $C_1$–$C_4$-halogenoalkyl-carbonyloxy-methyl having 1 to 3 fluorine, chlorine and/or bromine atoms, $C_1$–$C_4$-alkylthio-methyl, or represents phenyl, phenylalkyl having 1 or 2 carbon atoms in the alkyl moiety, phenylalkoxy having 1 or 2 carbon atoms in the alkoxy moiety or represents phenylmethyl-oxymethyl, where the four last mentioned radicals may be unsubstituted or mono- or disubstituted in the phenyl moiety by identical or different substituents from the group consisting of fluorine, chlorine, bromine, nitro, cyano, methyl, ethyl, methoxy, ethoxy, methylthio, ethylthio, chloromethyl, dichloromethyl, difluoromethyl, trifluoromethyl, trifluoromethoxy, trifluoromethylthio, methylsulfinyl, methylsulfonyl, methylcarbonyl, ethylcarbonyl, methoxycarbonyl and ethoxycarbonyl, or two geminal or vicinal $R^4$ radicals together with the carbon atoms to which they are attached represent a saturated or monounsaturated six-membered ring which may contain one or two non-adjacent oxygen atoms and which may be unsubstituted mono- or disubstituted by fluorine, chlorine, methyl, ethyl and/or methoxy, n represents 1 or 2, X represents a nitrogen atom or represents a grouping of the formula CH, CCl, CBr, C—CN, C—C≡CH or

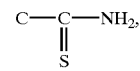

and

A represents a direct bond or represents a $CH_2$ group.

15. A compositions for controlling undesirable microorganisms and animal pest according to claim 4, wherein the animal pests are selected from the group consisting of insects, arachnids, nemtodes and mixtures thereof.

16. A method for controlling undesirable microorganisms and animal pests according to claim 5, wherein the animal pests are selected from the group consisting of insects, arachnids, nemtodes and mixtures thereof.

* * * * *